US007718684B2

(12) United States Patent
Jung et al.

(10) Patent No.: US 7,718,684 B2
(45) Date of Patent: May 18, 2010

(54) METHODS AND MATERIALS FOR ASSESSING PROSTATE CANCER THERAPIES AND COMPOUNDS

(75) Inventors: Michael E. Jung, Los Angeles, CA (US); Samedy Ouk, Los Angeles, CA (US); Charles L. Sawyers, Los Angeles, CA (US); Charlie D. Chen, Los Angeles, CA (US); Derek Welsbie, Northridge, CA (US)

(73) Assignee: The Regents of the University of California, Oakland, CA (US)

( * ) Notice: Subject to any disclaimer, the term of this patent is extended or adjusted under 35 U.S.C. 154(b) by 26 days.

(21) Appl. No.: 10/590,445

(22) PCT Filed: Feb. 23, 2005

(86) PCT No.: PCT/US2005/005529

§ 371 (c)(1),
(2), (4) Date: Aug. 24, 2006

(87) PCT Pub. No.: WO2005/099693

PCT Pub. Date: Oct. 27, 2005

(65) Prior Publication Data

US 2007/0191443 A1     Aug. 16, 2007
US 2008/0090888 A2     Apr. 17, 2008

Related U.S. Application Data

(60) Provisional application No. 60/547,101, filed on Feb. 24, 2004.

(51) Int. Cl.
A01N 43/50    (2006.01)
C07D 293/00   (2006.01)
C07D 409/00   (2006.01)

(52) U.S. Cl. .............. 514/385; 514/396; 514/397; 514/398; 514/520; 514/522; 558/413; 558/423; 548/100; 548/320.1; 548/321.1; 564/154; 564/155

(58) Field of Classification Search .............. 514/385, 514/396, 397, 398, 399, 400, 520, 522, 596; 548/100, 320.1, 321.1; 558/413, 428; 564/154, 564/155
See application file for complete search history.

(56) References Cited

U.S. PATENT DOCUMENTS 3,823,240 A    7/1974    Sauli (Continued)

FOREIGN PATENT DOCUMENTS

AU    217893    6/1958

(Continued)

OTHER PUBLICATIONS

Wallen et al., "Androgen Receptor Gene Mutations in Hormone-Refractory Prostate Cancer", J. Pathology 1999, vol. 189, pp. 559-563.

(Continued)

Primary Examiner—Ardin Marschel
Assistant Examiner—Savitha Rao
(74) Attorney, Agent, or Firm—Venable LLP; Michael A. Gollin; Lars H. Genieser

(57) ABSTRACT

A modest (2-5 fold) increase in androgen receptor (AR) mRNA is the only expression change consistently associated with developing resistance to antiandrogen therapy. Increased levels of AR confer resistance to anti-androgens by amplifying signal output from low levels of residual ligand and altering the normal response to antagonists. This invention provides cell based assays for use in the examination of new therapeutic modalities and provides for the design of novel antiandrogen compounds.

13 Claims, 2 Drawing Sheets

U.S. PATENT DOCUMENTS

| | | | |
|---|---|---|---|
| 3,984,430 | A | 10/1976 | Curran |
| 4,097,578 | A | 6/1978 | Perronnet et al. |
| 4,234,736 | A | 11/1980 | Bernauer et al. |
| 4,304,782 | A | 12/1981 | Dumont et al. |
| 4,312,881 | A | 1/1982 | Wootton |
| 4,399,216 | A | 8/1983 | Axel et al. |
| 4,407,814 | A | 10/1983 | Bernauer et al. |
| 4,427,438 | A | 1/1984 | Nagano et al. |
| 4,473,393 | A | 9/1984 | Nagpal |
| 4,482,739 | A | 11/1984 | Bernauer et al. |
| 4,559,157 | A | 12/1985 | Smith et al. |
| 4,608,392 | A | 8/1986 | Jacquet et al. |
| 4,749,403 | A | 6/1988 | Liebl et al. |
| 4,820,508 | A | 4/1989 | Wortzman |
| 4,859,228 | A | 8/1989 | Prisbylla |
| 4,873,256 | A | 10/1989 | Coussediere et al. |
| 4,938,949 | A | 7/1990 | Borch et al. |
| 4,944,791 | A | 7/1990 | Schröder et al. |
| 4,992,478 | A | 2/1991 | Geria |
| 5,010,182 | A | 4/1991 | Brake et al. |
| 5,069,711 | A | 12/1991 | Fischer et al. |
| 5,071,773 | A | 12/1991 | Evans et al. |
| 5,166,358 | A | 11/1992 | Seuron et al. |
| 5,411,981 | A | 5/1995 | Gaillard-Kelly et al. |
| 5,434,176 | A | 7/1995 | Claussner et al. |
| 5,556,983 | A | 9/1996 | Claussner et al. |
| 5,589,497 | A | 12/1996 | Claussner et al. |
| 5,614,620 | A | 3/1997 | Liao et al. |
| 5,627,201 | A | 5/1997 | Gaillard-Kelly et al. |
| 5,646,172 | A | 7/1997 | Claussner et al. |
| 5,656,651 | A | 8/1997 | Sovak et al. |
| 5,705,654 | A | 1/1998 | Claussner et al. |
| 5,726,061 | A | 3/1998 | Robbins et al. |
| 5,750,553 | A | 5/1998 | Claussner et al. |
| RE35,956 | E | 11/1998 | Gaillard-Kelly et al. |
| 5,958,936 | A | 9/1999 | Claussner et al. |
| 5,985,868 | A | 11/1999 | Gray |
| 6,087,509 | A * | 7/2000 | Claussner et al. ......... 548/307.1 |
| 6,107,488 | A | 8/2000 | Bouchet et al. |
| 6,235,910 | B1 | 5/2001 | Beller et al. |
| 6,242,611 | B1 | 6/2001 | Claussner et al. |
| 6,307,030 | B1 | 10/2001 | French et al. |
| 6,472,415 | B1 | 10/2002 | Sovak et al. |
| 6,479,063 | B2 | 11/2002 | Weisman et al. |
| 6,489,163 | B1 | 12/2002 | Roy et al. |
| 6,506,607 | B1 | 1/2003 | Shyjan |
| 6,828,471 | B2 | 12/2004 | Sawyers et al. |
| 6,949,521 | B2 * | 9/2005 | Chu et al. ..................... 514/45 |
| 7,271,188 | B2 | 9/2007 | Tachibana et al. |
| 2002/0133833 | A1 | 9/2002 | Sawyers et al. |
| 2004/0009969 | A1 | 1/2004 | Cleve et al. |
| 2004/0116417 | A1 | 6/2004 | Boubia et al. |
| 2005/0153968 | A1 | 7/2005 | Bi et al. |
| 2006/0127902 | A1 | 6/2006 | Madden et al. |
| 2007/0249697 | A1 | 10/2007 | Tachibana et al. |

FOREIGN PATENT DOCUMENTS

| | | | |
|---|---|---|---|
| DE | 2102605 | | 7/1971 |
| EP | 0017976 | A2 | 10/1980 |
| EP | 0017976 | A3 | 10/1980 |
| EP | 0017976 | B1 | 6/1983 |
| EP | 0 002 259 | B1 | 10/1984 |
| EP | 0331232 | A2 | 9/1989 |
| EP | 362179 | | 4/1990 |
| EP | 0 494 819 | A1 | 1/1992 |
| EP | 0 578 516 | A1 | 5/1993 |
| EP | 0 580 459 | A1 | 5/1993 |
| EP | 0572191 | A1 | 12/1993 |
| EP | 0 580 459 | B1 | 1/1994 |
| EP | 0 721 944 | B1 | 1/2001 |
| EP | 1 790 640 | A | 5/2007 |
| FR | 2 693 461 | A1 | 1/1994 |
| FR | 2 715 402 | A1 | 1/1994 |
| FR | 2 845 384 | A1 | 10/2002 |
| JP | 2019363 | A | 1/1990 |
| WO | WO 90/13646 | | 11/1990 |
| WO | WO 97/00071 | | 1/1997 |
| WO | WO 97/19064 | | 5/1997 |
| WO | WO 97/19931 | | 6/1997 |
| WO | WO 00/17163 | | 3/2000 |
| WO | WO 02/053155 | A1 | 7/2002 |
| WO | WO 02/081453 | A1 | 10/2002 |
| WO | WO 03/029245 | A1 | 4/2003 |
| WO | WO 03/057220 | A1 | 7/2003 |
| WO | WO 03/093243 | A1 | 11/2003 |
| WO | WO 03/096980 | | 11/2003 |
| WO | WO 2004/031160 | A2 | 4/2004 |
| WO | WO 2004/070050 | A2 | 8/2004 |
| WO | WO 2005/059109 | | 6/2005 |
| WO | WO 2005/060661 | | 7/2005 |
| WO | WO 2005/089752 | | 9/2005 |
| WO | WO 2006/010642 | | 2/2006 |
| WO | WO 2006/028226 | A1 | 3/2006 |
| WO | WO 2006/124118 | | 11/2006 |
| WO | WO 2006/124118 | A1 | 11/2006 |
| WO | WO 2007/126765 | | 11/2007 |
| WO | WO 2007/127010 | | 11/2007 |
| WO | WO 2008/119015 | A2 | 10/2008 |

OTHER PUBLICATIONS

Lu et al. "Molecular Mechanisms of Androgen-Independent Growth of Human Prostate Cancer LNCaP-Al Cells", Endocrinology 1999, vol. 140, No. 11, pp. 5054-5059.

Ausubel et al., Current Protocols in Molecular Biology, Wiley Interscience Publishers, (1995).

Sambrook et al., Molecular Cloning: A Laboratory Manual $2^{nd}$ edition (1989) Cold Spring Harbor Laboratory Press, Cold Spring Harbor, N.Y.

Chang et al. Science 240 (4850), 324-326 (1988).

NM_000044<http://www.ncbi.nlm.nih.gov:80/entrez/viewer.fcgi?cmd=Retrieve&db=nucleotide&list_uids=21322251&dopt=GenBank&term=sapiens+AR+androgen+receptor+prostate+cancer&qty=1>gi:21322251, printed Oct. 24, 2007.

*Mammalian Cell Biotechnology: a Practical Approach*, M. Butler, ed. (IRL Press, 1991).

Keown et al., *Methods in Enzymology*, 185:527-537 (1990).

Mansour et al., *Nature*, 336:348-352 (1988).

Muller et al., 1991, Mol. & Cell. Bio. 11:1785.

Urlaub et al., *Proc. Natl. Acad. Sci. USA*, 77:4216 (1980).

Stinchcomb et al., *Nature*, 282:39 (1979).

Kingsman et al., *Gene*, 7: 141 (1979).

Tschumper et al., *Gene*, 10: 157 (1980).

Jones, *Genetics*, 85:12 (1977).

Feldman, B.J. & Feldman, D. The development of androgen-independent prostate cancer. Nat Rev Cancer 1, 34-45 (2001).

Gelmann, E.P. Molecular biology of the androgen receptor. J Clin Oncol 20, 3001-15 (2002).

Balk, S. P. Androgen receptor as a target in androgen-independent prostate cancer. Urology 60, 132-8; discussion 138-9 (2002).

Taplin, M.E. et al. Selection for androgen receptor mutations in prostate cancers treated with androgen antagonist. Cancer Res 59, 2511-5 (1999).

Taplin, M.E. et al. Androgen receptor mutations in androgen-independent prostate cancer: Cancer and Leukemia Group B Study 9663. J Clin Oncol 21, 2673-8 (2003).

Visakorpi, T. et al. In vivo amplification of the androgen receptor gene and progression of human prostate cancer. Nat Genet 9, 401-6 (1995).

Taplin, M.E. et al. Mutation of the androgen-receptor gene in metastatic androgen-independent prostate cancer. N Engl J Med 332, 1393-8 (1995).

Veldscholte, J. et al. A mutation in the ligand binding domain of the androgen receptor of human LNCaP cells affects steroid binding characteristics and response to anti-androgens. Biochem Biophys Res Commun 173, 534-40 (1990).

Matias, P.M. et al. Structural basis for the glucocorticoid response in a mutant human androgen receptor (AR(ccr)) derived from an androgen-independent prostate cancer. J Med Chem 45, 1439-46 (2002).

Craft, N., Shostak, Y., Carey, M. & Sawyers, C.L. A mechanism for hormone-independent prostate cancer through modulation of androgen receptor signaling by the HER-2/neu tyrosine kinase. Nat Med 5, 280-5 (1999).

Gioeli, D. et al. Androgen receptor phosphorylation. Regulation and identification of the phosphorylation sites. J Biol Chem 277, 29304-14 (2002).

Kato, S. et al. Activation of the estrogen receptor through phosphorylation by mitogen-activated protein kinase. Science 270, 1491-4 (1995).

Font de Mora, J. & Brown, M. AlB1 is a conduit for kinase-mediated growth factor signaling to the estrogen receptor. Mol Cell Biol 20, 5041-7 (2000).

Tremblay, A., Tremblay, G.B., Labrie, F. & Giguere, V. Ligand-independent recruitment of SRC-1 to estrogen receptor beta through phosphorylation of activation function AF-1. Mol Cell 3, 513-9 (1999).

Gregory, C.W. et al. A mechanism for androgen receptor-mediated prostate cancer recurrence after androgen deprivation therapy. Cancer Res 61, 4315-9 (2001).

Li, P. et al. Heterogeneous expression and functions of androgen receptor co-factors in primary prostate cancer. Am J Pathol 161, 1467-74 (2002).

Glass, C.K. & Rosenfeld, M.G. The coregulator exchange in transcriptional functions of nuclear receptors. Genes Dev 14, 121-41 (2000).

Raffo, A.J. et al. Overexpression of bcl-2 protects prostate cancer cells from apoptosis in vitro and confers resistance to androgen depletion in vivo. Cancer Res 55, 4438-45 (1995).

McDonnell, T.J. et al. Expression of the protooncogene bcl-2 in the prostate and its association with emergence of androgen-independent prostate cancer. Cancer Res 52, 6940-4 (1992).

Kinoshita, H. et al. Methylation of the androgen receptor minimal promoter silences transcription in human prostate cancer. Cancer Res 60, 3623-30 (2000).

Shang, Y., Myers, M. & Brown, M. Formation of the androgen receptor transcription complex. Mol Cell 9, 601-10 (2002).

Zhau, H.Y. et al. Androgen-repressed phenotype in human prostate cancer. Proc Natl Acad Sci U S A 93, 15152-7 (1996).

Wainstein, M.A. et al. CWR22: androgen-dependent xenograft model derived from a primary human prostatic carcinoma. Cancer Res 54, 6049-52 (1994).

Ellis, W.J. et al. Characterization of a novel androgen-sensitive, prostate-specific antigen-producing prostatic carcinoma xenograft: LuCaP 23. Clin Cancer Res 2, 1039-48 (1996).

Horoszewicz, J.S. et al. LNCaP model of human prostatic carcinoma. Cancer Res 43, 1809-18 (1983).

Klein, K.A. et al. Progression of metastatic human prostate cancer to androgen independence in immunodeficient SCID mice. Nat Med 3, 402-8 (1997).

Perou, C.M. et al. Molecular portraits of human breast tumors. Nature 406, 747-52 (2000).

Gregory, C.W., Johnson, R.T., Jr., Mohler, J.L., French, F.S. & Wilson, E.M. Androgen receptor stabilization in recurrent prostate cancer is associated with hypersensitivity to low androgen. Cancer Res 61, 2892-8. (2001).

Huang, Z.Q., Li, J. & Wong, J. AR possess an intrinsic hormone-independent transcriptional activity. Mol Endocrinol 16, 924-37 (2002).

Matias, P.M. et al. Structural evidence for ligand specificity in the binding domain of the human androgen receptor. Implications for pathogenic gene mutations. J Biol Chem 275, 26164-71 (2000).

Lobaccaro, J.M. et al. Molecular modeling and in vitro investigations of the human androgen receptor DNA-binding domain: application for the study of two mutations. Mol Cell Endocrinol 116, 137-47 (1996).

Migliaccio, A. et al. Steroid-induced androgen receptor-oestradiol receptor beta-SRC complex triggers prostate cancer cell proliferation. Embo J 19, 5406-17 (2000).

Kousteni, S. et al. Nongenotropic, sex-nonspecific signaling through the estrogen or androgen receptors: dissociation from transcriptional activity. Cell 104, 719-30 (2001).

Manolagas, S.C., Kousteni, S. & Jilk a, R.L. Sex steroids and bone. Recent Prog Horm Res 57, 385-409 (2002).

DePrimo, S.E. et al. Transcriptional programs activated by exposure of human prostate cancer cells to androgen. Genome Biol 3, Research0032 (2002).

Masiello, D., Cheng, S., Bubley, G.J., Lu, M.L. & Balk, S.P. Bicalutamide functions as an androgen receptor antagonist by assembly of a transcriptionally inactive receptor. J Biol Chem 277, 26321-6 (2002).

Edwards, J., Krishna, N.S., Grigor, K.M. & Bartlett, J.M. Androgen receptor gene amplification and protein expression in hormone refractory prostate cancer. Br J Cancer 89, 552-6 (2003).

Laitinen, S., Karhu, R., Sawyers, C.L., Vessella, R.L. & Visakorpi, T. Chromosomal aberrations in prostate cancer xenografts detected by comparative genomic hybridization. Genes Chromosomes Cancer 35, 66-73 (2002).

Grad, J.M., Dai, J.L., Wu, S. & Burnstein, K.L. Multiple androgen response elements and a Myc consensus site in the androgen receptor (AR) coding region are involved in androgen-mediated up-regulation of AR messenger RNA. Mol Endocrinol 13, 1896-911 (1999).

Craft, N. et al. Evidence for clonal outgrowth of androgen-independent prostate cancer cells from androgen-dependent tumors through a two-step process. Cancer Res 59, 5030-6 (1999).

Ellwood-Yen, K. et al. Myc-driven murine prostate cancer shares molecular features with human prostate tumors. Cancer Cell 4, 223-38 (2003).

Wang, S. et al. Prostate-specific deletion of the murine Pten tumor suppressor gene leads to metastatic prostate cancer. Cancer Cell 4, 209-21 (2003).

Shiau, A.K. et al. The structural basis of estrogen receptor/coactivator recognition and the antagonism of this interaction by tamoxifen. Cell 95, 927-37 (1998).

Norris, J.D. et al. Peptide antagonists of the human estrogen receptor. Science 285, 744-6 (1999).

Baek, S.H. et al. Exchange of N-CoR corepressor and Tip60 coactivator complexes links gene expression by NF-kappaB and beta-amyloid precursor protein. Cell 110, 55-67 (2002).

Shang, Y. & Brown, M. Molecular determinants for the tissue specificity of SERMs. Science 295, 2465-8 (2002).

Schellhammer, P.F. et al. Prostate specific antigen decreases after withdrawal of antiandrogen therapy with bicalutamide or flutamide in patients receiving combined androgen blockade. J Urol 157, 1731-5 (1997).

Sack, J.S. et al. Crystallographic structures of the ligand-binding domains of the androgen receptor and its T877A mutant complexed with the natural agonist dihydrotestosterone. Proc Natl Acad Sci U S A 98, 4904-9 (2001).

Zhou, Z.X., Sar, M., Simental, J.A., Lane, M.V. & Wilson, E.M. A ligand-dependent bipartite nuclear targeting signal in the human androgen receptor. Requirement for the DNA-binding domain and modulation by NH2-terminal and carboxyl-terminal sequences. J Biol Chem 269, 13115-23 (1994).

Chen, C.D., Welsbie, D.S., Tran, C., Baek, S.H., Chen, R., Vessella, R., Rosenfeld, M.G., and Sawyers, C.L., Molecular determinants of resistance to antiandrogen therapy, Nat. Med., 10: 33-39, 2004.

*The Pharmacological Basis of Therapeutics*, Goodman and Gilman, eds., Macmillan Publishing Co., New York.

The Practice of Medicinal Chemistry, Camille G. Wermuth et al., Ch 31, (Academic Press, 1996).

Design of Prodrugs, edited by H. Bundgaard, (Elsevier, 1985).

A Textbook of Drug Design and Development, P. Krogsgaard-Larson and H. Bundgaard, eds. Ch 5, pp. 113-191 (Harwood Academic Publishers, 1991).

Remington: The Science and Practice of Pharmacy, 19$^{th}$ Edition, Gennaro (ed.) 1995, Mack Publishing Company, Easton, PA.

Teutsch, G.; Goubet, F.; Battmann, T.; Bonfils, A.; Bouchoux, F.; Cerede, E.; Gofflo, D.; Gaillard-Kelly, M.; Philibert. D. .*J. Steroid Biochem. Molec. Biol*. 1994, 48, 111-119.

Van Dort, M. E.; Robins, D. M.; Wayburn, B. *J. Med. Chem.* 2000, 43, 3344-3347.

Homma,S., et al., "Differential levels of human leukocyte antigen-class I, multidrug-resistance 1 and androgen receptor expressions in untreated prostate cancer cells: the robustness of prostate cancer", Oncol. Rep. 18 (2), 343-346 (2007).

Cai,C., et al., "c-Jun has multiple enhancing activities in the novel cross talk between the androgen receptor and Ets variant gene 1 in prostate cancer", Mol. Cancer Res. 5 (7), 725-735 (2007).

Su,Q.R., et al., "Polymorphisms of androgen receptor gene in childhood and adolescent males with first-onset major depressive disorder and associationwith related symptomatology", Int. J. Neurosci. 117 (7), 903-917 (2007).

Brockschmidt,F.F., et al., "The two most common alleles of the coding GGN repeat in the androgen receptor gene cause differences in protein function", J. Mol. Endocrinol. 39 (1), 1-8 (2007).

Hamilton-Reeves,J.M., et al, "Isoflavone-rich soy protein isolate suppresses androgen receptor expression without altering estrogen receptor-beta expression or serum hormonal profiles in men at high risk of prostate cancer", J. Nutr. 137 (7), 1769-1775 (2007).

Sweet,C.R., et al., "A unique point mutation in the androgen receptor gene in a family with complete androgen insensitivity syndrome", Fertil. Steril. 58 (4), 703-707 (1992).

Batch,J.A., et al., "Androgen receptor gene mutations identified by SSCP in fourteen subjects with androgen insensitivity syndrome", Hum. Mol. Genet. 1 (7), 497-503 (1992).

Wooster,R., et al., "A germline mutation in the androgen receptor gene in two brothers with breast cancer and Reifenstein syndrome", Nat. Genet. 2 (2), 132-134 (1992).

Saunders,P.T., et al., "Point mutations detected in the androgen receptor gene of three men with partial androgen insensitivity syndrome", Clin. Endocrinol. (Oxf) 37 (3), 214-220 (1992).

Zoppi,S., et al. "Amino acid substitutions in the DNA-binding domain of the human androgen receptor are a frequent cause of receptor-binding positive androgen resistance", Mol. Endocrinol. 6 (3), 409-415 (1992).

Wang, Long G., et al., "Overexpressed androgen receptor linked to p21WAF1 silencing may be responsible for androgen independence and resistance to apoptosis of a prostate cancer cell line", Cancer Research 61 (20), pp. 7544-7551 (Oct. 15, 2001).

Shi, Xu-Bao, et al., "Functional analysis of 44 mutant androgen receptors from human prostate cancer", Cancer Research 62 (5), pp. 1496-1502 (Mar. 1, 2002).

Navone, N. M., et al., "Model Systems of Prostate Cancer: Uses and Limitations" Cancer Metastasis, Kluwer Academic Publishers, Dordrecht, NL, 17 (4), 1999, pp. 361-371.

Singh et al., "*Androgen Receptor Antagonists (Antiandrogens): Structure-Activity Relationships*", Current Medicinal Chemistry, 2000, 7, pp. 211-247.

Bohl et al., "*Structural basis for antagonism and resistance of bicalutamide in prostate cancer*", Proc. Nat. Acad. Sci., 2005, v. 102(17), pp. 6201-6206.

Nam et al., "*Action of the Src Family Kinase Inhibitor, Dasatinib (BMS-354825), on Human Prostate Cancer Cells*", Cancer Res., 2005, v. 65(20), pp. 9185-9189.

Burnstein et al. Androgen Glucocorticoid Regulation of Androgen Receptor cDNA Expression. *Molecular and Cellular Endocrinology*. 1995. v. 115, pp. 177-186.

Cinar et al. Androgen Receptor Mediates the Reduced Tumor Growth, Enhanced Androgen Responsiveness, and Selected Target Gene Transactivation in Human Prostate Cancer Cell Line. *Cancer Research*. 2001. v. 61. pp. 7310-7317.

Szelei et al. Androgen-Induced Inhibition of Proliferation in Human Breast Cancer MCF7 Cells Transfected with Androgen Receptor. Endocrinology. 1999. v. 138 (4). pp. 1406-1412.

Raffo et al. Overexpression of bcl-2 Protects Prostate Cancer Cells from Apoptosis in Vitro and Confers Resistance to Androgen Depletion in vivo. Cencer Research. 1995. v. 55. 4438-4445.

Office Action of Aug. 11, 2009 from U.S. Patent and Trademark Office for U.S. Appl. No. 10/583,280.

P.J. Creaven et al., "Pharmacokinetics and Metabolism of Nilutamide", Supp. Urology, vol. 37, No. 2 (Feb. 1991) pp. 13-19.

International Search Report issued in PCT Application No. PCT/US06/11417 dated Jul. 3, 2006.

Extended European Search Report issued in European Patent Application No. EP 06748863.5, mailed on Feb. 12, 2009.

International Search Report issued in International Application No. PCT/US2007/007854, mailed on Apr. 15, 2008.

Written Opinion issued in International Application No. PCT/US2007/007854, mailed on Apr. 15, 2008.

S.Ouk et al., "Development Of Androgen Receptor Inhibitors for Hormone-refractory Prostate Cancer", Prostate Cancer Foundation Meeting, Scottsdale, AZ, Sep. 29-Oct. 1, 2005.

Cousty-Berlin, et al., "Preliminary Pharmacokinetics and Metabolism of Novel Non-steroidal Antiandrogens in the Rat: Relation of their Systemic Activity to the Formation of a Common Metabolite," *J. Steroid Biochem. Molec. Biol.*, vol. 51, No. 1/2, pp. 47-55 (1994).

Feher, et al., "BHB: A Simple Knowledge-Based Scoring Function to Improve the Efficiency of Database Screening," *J. Chem. Inf. Comput. Sci.*, vol. 43, pp. 1316-1327 (2003).

Foury, et al., "Control of the Proliferation of Prostate Cancer Cells by an Androgen and Two Antiandrogens. Cell Specific Sets of Responses," *J. Steroid Biochem. Molec. Biol.*, vol. 66, No. 4, pp. 235-240 (1998).

Goubet, et al., Conversion of a Thiohydantoin to he Corresponding Hydantoin via a Ring-Opening/Ring Closure Mechanism, *Tetrahedron Letters*, vol. 37, No. 43, pp. 7727-7730 (1996).

Karvonen, et al., "Interaction of Androgen Receptors with Androgen Response Element in Intact Cells," *The Journal of Biological Chemistry*, vol. 272, No. 25, pp. 15973-15979 (1997).

Kemppainen, et al., "Distinguishing Androgen Receptor Agonists and Antagonists: Distinct Mechanisms of Activation by Medroxyprogesterone Acetate and Dihydrotestosterone," *Mol. Endocrinol.*, vol. 13, pp. 440-454 (1999); mend.endojournals.org.

Marhefka, et al., "Homology Modeling Using Multiple Molecular Dynamics Simulations and Docking Sudies of the Human Androgen Receptor Ligand Binding Domain Bound to Testosterone and Nonsteroidal Ligands," *J. Med. Chem.*, vol. 44, No. 11, pp. 1729-1740 (2001).

Matias, et al., "Local Inhibition of Sebaceous Gland Growth by Topically Applied RU 58841," *NY Acad. Sci.*, vol. 761, pp. 56-65 (1995).

Sderholm, et al., "Three-Dimensional Structure—Activity Relationships of Nonsteroidal Ligands in Complex with Androgen Receptor Ligand-Binding Domain," *J. Med. Chem.*, vol. 48, No. 4, pp. 917-925 (2005).

Sperry, et al., Androgen binding profiles of two distinct nuclear androgen receptors in Atlantic croaker (*Micropogonias undulates*), *Journal of Steroid Biochemistry & Molecular Biology*, vol. 73, pp. 93-103 (2000).

Zarghami, et al., "Steroid hormone regulation of prostate-specific antigen gene expression in breast cancer," *British Journal of Cancer*, vol. 75, No. 4, pp. 579-588 (1997).

International Search Report issued in PCT Application PCT/US2007/07485, mailed on Sep. 4, 2008.

Written Opinion issued in PCT Application PCT/US2007/07485, mailed on Sep. 4, 2008.

International Search Report issued in International Application No. PCT/US2008/012149 mailed on Apr. 29, 2009.

Written Opinion issued in International Application No. PCT/US2008/012149, mailed on Apr. 29, 2009.

Office Action issued in U.S. Appl. No. 10/590,445, mailed on Mar. 2, 2009.

International Search Report issued in International Application No. PCT/US2007/007854, mailed on Apr. 15, 2008.

Written Opinion issued in International Application No. PCT/US2007/007854, mailed on Apr. 15, 2008.

International Search Report issued in PCT Application No. PCT/US2004/042221, mailed on Jun. 20, 2005.

Written Opinion issued in PCT Application No. PCT/US2004/042221, mailed on Jun. 20, 2005.

Written Opinion issued in PCT Application No. PCT/US2005/005529, mailed on Nov. 10, 2005.

Written Opinion issued in PCT Application No. PCT/US2006/011417, mailed on Jul. 3, 2006.

Data Sheet from U.S. Patent and Trademark Office (USPTO) File Wrapper for U.S. Appl. No. 08/807,760.

Notice of References Cited from U.S. Patent and Trademark Office (USPTO) File Wrapper for U.S. Appl. No. 08/807,760.

Office Action of Jan. 18, 1994 from U.S. Patent and Trademark Office for U.S. Appl. No. 08/064,257.

Office Action (paper No. 7) from U.S. Patent and Trademark Office for U.S. Appl. No. 08/064,257.

Office Action (paper No. 10) from U.S. Patent and Trademark Office for U.S. Appl. No. 08/064,257.

Office Action of Aug. 14, 1992 from U.S. Patent and Trademark Office for U.S. Appl. No. 07/819,110.

Notice of References Cited of Jul. 24, 1992 from U.S. Patent and Trademark Office for U.S. Appl. No. 07/819,110.

Office Action of Feb. 22, 1993 from U.S. Patent and Trademark Office for U.S. Appl. No. 07/819,110.

Office Action of Sep. 2, 1993 from U.S. Patent and Trademark Office for U.S. Appl. No. 07/819,110.

Office Action of Jun. 1, 1994 from U.S. Patent and Trademark Office for U.S. Appl. No. 07/819,110.

M.J. Linja et al., "Amplification and overexpression of androgen receptor gene in hormone-refractory prostate cancer", Cancer Research, vol. 61 (May 1, 2001) pp. 3550-3555.

J. Holzbeierlein et al., "Gene Expression Analysis of Human Prostate Carcinoma during Hormonal Therapy Identifies Androgen-Responsive Genes and Mechanisms of Therapy Resistance", Am. J. Pathology, vol. 164, No. 1 (Jan. 2004) pp. 217-227.

C.D. Chen et al., "Molecular determinants of resistance to antiandrogen therapy", Nature Medicine, vol. 10, No. 1 (Jan. 2004) pp. 33-39.

Office Action of Jul. 23, 2008 from U.S. Patent and Trademark Office for U.S. Appl. No. 10/590,445.

Karp et al., "Prostate Cancer Prevention: Investigational Approaches and Opportunities", Cancer Res., v. 56 (Dec. 15, 1996) pp. 5547-5556.

Graham and van der Eb, "A new technique for the assay of infectivity of human adenovirus 5 DNA", Virology, v. 52(2) (Apr. 1973) pp. 456-467.

WO2005/059109 A3 (International Search Report), Jun. 30, 2005, The Regents of the University of California.

A.M. Soto et al., "Control of Cell Proliferation: Evidence for Negative Control on Estrogen-sensitive T47D Human Breast Cancer Cells", Cancer Research, 46, (1986), pp. 2271-2275.

J. Szelei et al., "Androgen-Induced Inhibition of Proliferation in Human Breast Cancer MCF7 Cells Transfected with Androgen Receptor", Endocrinology, 138(4), (1997) pp. 1406-1412.

Jones, *Genetics*, 85:23 (1977).

International Search Report dated Oct. 28, 2005, issued in PCT/US05/05529.

\* cited by examiner

METHODS AND MATERIALS FOR ASSESSING PROSTATE CANCER THERAPIES AND COMPOUNDS

This application is the National Stage of International Application No. PCT/US2005/005529, filed Feb. 23, 2005, which claims the benefit of U.S. Provisional Application No. 60/547,101, filed Feb. 24, 2004. This invention was made with United States Government support under Grant No. DAMD17-98-1-8569 awarded by the U.S. Army. The Government has certain rights in this invention.

BACKGROUND OF THE INVENTION

1. Field of the Invention

The present invention relates to methods and materials for assessing prostate cancer therapies, as well as novel prostate cancer compositions and methods for making and using said compositions.

2. Description of Related Art

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In this century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastaic disease from a carcinoma is fatal. Moreover, even for those cancer patients who initially survive their primary cancers, common experience has shown that their lives are dramatically altered.

Adenocarcinoma of the prostate is the most frequently diagnosed cancer in men in the United States, and is the second leading cause of male cancer deaths (Karp et al., Cancer Res. 56:5547-5556 (1996)). Therapy for prostate cancer is typically initiated using hormone drugs that lower serum testosterone, often given in combination with competitive androgen receptor (AR) antagonists. Although initially effective at blocking tumor growth, these therapies eventually fail, leading to a drug resistant stage called androgen independent or hormone refractory (HR) disease that is uniformly lethal.

Postulated mechanisms to explain resistance to hormone therapy can be separated into three general categories.[1-3] The first includes DNA-based alterations in the AR gene such as amplification or point mutations, which collectively only occur in a minority of patients.[4-7] A subset of these AR mutations map to the ligand binding domain (LBD) and are proposed to cause resistance by altering the response of the receptor such that noncanonical ligands like estrogen or hydrocortisone, or even AR antagonists like flutamide, behave as agonists.[8,9] Although their clinical association with antiandrogen resistance is strong, the overall frequency of AR amplification or mutation cannot account for most cases of hormone refractory disease.

The second category applies to the majority of patients without AR gene mutation or amplification who retain active AR signaling. Increased mitogen-activated protein kinase signaling mediated by oncogenes such as ErbB2 or Ras can cause ligand-independent activation of AR.[10,11] The kinases and substrates responsible for AR activation in this setting are unknown, but this is presumed to occur through downstream phosphorylation of AR-associated proteins or AR itself, analogous to the estrogen receptor (ER).[12-14] Similarly, alteration in the balance of coactivators or corepressors can affect AR activation,[15-16] based on similar findings for ER.[17] The relative frequency of these events and their relationship to clinical drug resistance remain to be define.

The third category of hormone resistance mechanisms is based on the concept that the pro-growth and survival functions of AR can be "bypassed" by alternative signaling pathways, such that AR is no longer relevant to disease progression. One example is upregulation of the anti-apoptotic gene Bcl-2 in late stage clinical samples,[18,19] but functional proof of a role in hormone resistance is lacking. The AR bypass hypothesis is also consistent with observations of AR gene methylation leading to decreased or absent AR expression in some HR cancers,[20] as well as reports that androgen induces growth arrest or apoptosis in certain contexts.[21,22]

Collectively, these data implicate multiple mechanisms by which prostate cancers acquire resistance to hormone therapy and highlight the continuing debate about the role of AR in late stage disease progression. Consequently, there is a need in the art for models that reproduce clinically significant aspects of this disease progression, particularly the transition from the initial stage in the prostate cancer where the cancer cells are sensitive to hormone antagonists to the subsequent drug resistant stage. In particular, a well-defined and manipulatable cell based model is needed to dissect the molecular events associated with the progression from a drug sensitive to a drug resistant phase. There is also a need in the art for cell based prostate cancer models that reproduce the drug sensitive and/or drug resistant phases of cancers of the prostate that can be used, for example in the evaluation of new therapeutic modalities. In addition, there is need for the identification of novel compounds that can be used to inhibit the growth of prostate cancer cells, particularly hormone refractory prostate cancers. The present invention disclosed herein satisfies this need.

SUMMARY OF THE INVENTION

Using microarray-based profiling of isogenic prostate cancer xenograft models, we found that a modest (2-5 fold) increase in androgen receptor (AR) mRNA was the only expression change consistently associated with developing resistance to antiandrogen therapy. This increase in AR mRNA and protein was both necessary and sufficient to convert prostate cancer growth from a hormone sensitive to hormone refractory stage, and was dependent on a functional ligand-binding domain. Furthermore, AR antagonists displayed agonist activity in cells with increased AR levels, and this antagonist/agonist conversion was associated with alterations in the pattern of coactivators and corepressors recruited to the promoter of AR target genes. Increased levels of AR confer resistance to anti-androgens by amplifying signal output from low levels of residual ligand and altering the normal response to antagonists. The disclosure provided herein that is based upon these findings includes assays for examining the effects of therapeutic compounds on mammalian cells such as androgen independent prostate cancer cells and further provides insight toward the design of novel antiandrogens.

One embodiment of the invention is a method of testing compounds for an effect on a mammalian prostate cancer cell comprising contacting the compound to be tested with a mammalian prostate cancer cell wherein the mammalian cancer cell is selected for the test because it expresses an exogenous wild type androgen receptor (AR) polynucleotide that encodes the AR polypeptide such that the levels of mRNA in the cell that encode the AR polypeptide or AR polypeptide are at least about 2 fold higher than normal/endogenous AR mRNA or AR polypeptide levels in a mammalian prostate cell; and then comparing one or more characteristics of the mammalian prostate cancer cell to which the compound was administered with the same one or more characteristics of a control mammalian prostate cancer cell to which the compound has not been administered, wherein a difference in one or more of the one or more characteristics indicates that the compound has an effect on the mammalian prostate cancer cell.

Another embodiment of the invention is a method of examining the physiological effect of a compound on a mammalian prostate cancer cell, the method comprising contacting the compound to be tested with a mammalian prostate cancer cell, wherein the mammalian prostate cancer cell is selected for the method because it expresses either an exogenous wild type polynucleotide that encodes the AR polypeptide or a polynucleotide that encodes a variant of the AR polypeptide, wherein the variant has a deletion, insertion or substitution of at least one amino acid in the AR polypeptide amino acid sequence and wherein the total levels of mRNA in the cell that encode the AR polypeptide variant or the total levels of AR polypeptide variant are at least 2 fold higher than normal/endogenous AR mRNA or AR polypeptide in the cell; and then examining one or more physiological characteristics of the mammalian prostate cancer cell to which the compound is administered, so that the physiological effect of the compound on the mammalian prostate cancer cell is examined.

A related embodiment of the invention is a method further comprising examining the physiological effect of a plurality of compounds on a mammalian prostate cancer cell selected as described above, wherein an observable difference in one or more physiological characteristics exerted by a first compound as compared to one or more physiological characteristics exerted by a second compound indicates that the first compound has a stronger or weaker physiological effect than the second compound on the mammalian prostate cancer cell. Typically the method is performed in a high throughput format. Alternatively, the method is performed in a low throughput format. Compounds tested in such assays are typically antagonists or agonists. In practice we define a drug as an AR antagonist when the drug inhibits or competes for the binding of a ligand or a stimulus and inhibits the biological function of the androgen receptor. A drug is defined as an AR agonist when the drug stimulates or activates the biological function of the androgen receptor.

Yet another embodiment of the invention is a method of testing one or more compounds for an effect on a mammalian cell, the method comprising contacting at least one compound to be tested with the mammalian cell, wherein the mammalian cell is selected for the test because it expresses an exogenous wild type or mutated protein of interest, such as the estrogen receptor, such that the total levels of mRNA in the cell that encode the protein of interest or the total protein levels of the protein of interest are at least 2 fold higher than normal/endogenous mRNA or polypeptide of the protein of interest, such as the estrogen receptor, in the cell, comparing one or more characteristics of the mammalian cell to which the compound is administered with the same one or more characteristics of a control mammalian cell to which the compound has not been administered, wherein a difference in one or more characteristics indicates that the compound has an effect on the mammalian cancer cell or mammalian cell. In such methods, the mammalian cell is typically a cancer cell, for example a breast, ovarian or prostate cancer cell.

A related embodiment of the invention is a method further comprising examining the physiological effect of a plurality of compounds on a mammalian cell that is selected as described above, wherein an observable difference in one or more physiological characteristics exerted by a first compound as compared to one or more physiological characteristics exerted by a second compound indicates that the first compound has a stronger or weaker physiological effect than the second compound on the mammalian cell.

Another embodiment of the invention is a method of treating a hormone refractory prostate cancer in a patient, the method comprising administering to the patient an agent that decreases or affects the biological function of the androgen receptor by affecting the androgen receptor ligand-binding, nuclear translocation, or by affecting DNA-binding, or through altering formation of coactivator or corepressor complexes associated with the androgen receptor.

Another embodiment of the invention is a method of treating a hormone refractory prostate cancer in a patient, the method comprising administering to the patient and an agent that decreases or affects the biological function of the androgen receptor through affecting the androgen receptor DNA levels, androgen mRNA levels, or androgen protein levels. In such methods, the androgen receptor protein level can be decreased through modulation of signal transduction pathways such as targeting EGF receptors that crosstalk to the androgen receptor. Alternatively, the androgen receptor protein level is decreased by the induction of cellular degradation pathways such as proteosome degradation machinery. Alternatively, the androgen receptor protein level is decreased by dissociating the androgen receptor from heat shock proteins that maintain the androgen receptor integrity. Preferably the androgen receptor protein level is decreased using androgen receptor antisense or mRNA knockdown technology. We consider that any one of these above manipulations or combination of any of these manipulations would affect the biological function of the androgen receptor. The preferred way of these methods would be to use an agent to disrupt or reduce the ligand binding of the androgen receptor.

Another embodiment of the invention is a method of treating a hormone refractory prostate cancer in a patient, the method comprising administering to the patient an agent that decreases or affects the biological function of the androgen receptor through modifying the androgen receptor protein. Optionally, the androgen receptor protein is modified by modifying the polynucleotide or polypeptide sequence of the androgen receptor or by posttranslational modifications of the androgen receptor including, but not restricted to, phosphorylation, acetylation, ubiquitination, and sumolation.

Another embodiment of the invention is a method of treating a disease or condition, which is resistant to a drug, or a treatment, or combination of a drug and a treatment by increasing the concentration of the protein that is the target of the drug or treatment, the method comprising administering one or more agents or utilizing a technique that affects the biological function of the protein through means described in the paragraphs above. Typically the disease or condition is hormone refractory prostate cancer, in which the androgen receptor DNA, mRNA, or protein levels is increased in prostate cancer cells after surgical or medical castration, or treatments with anti-androgen therapy, or the combination of castration and anti-androgen therapy. In an illustrative embodiment, the disease or condition is hormone refractory breast cancer, in which the estrogen receptor DNA, mRNA, or protein levels is increased in breast cancer cells after hormone therapy such as treatments with tamoxifen or raloxifene.

Yet another embodiment of the invention is a method of inhibiting prostate specific antigen production in a mammalian prostate cancer cell (e.g. a hormone refractory prostate cancer), the method comprising contacting the cell with a composition comprising a compound selected from the group consisting of compounds 4 and 5 shown in Example 6, so that prostate specific antigen production in the prostate cancer cell is inhibited. A related embodiment of the invention is method of inhibiting the growth of a human prostate cancer cell, the method comprising contacting the cell with a composition comprising a compound selected from the group consisting of compounds 4 and 5 shown in Example 6, such that growth of the prostate cancer cell is inhibited. Another related embodiment of the invention is a method of antagonizing the function of the ligand binding domain of the AR polypeptide in a prostate cancer cell, the method comprising contacting the cell with a compound selected from the group consisting of compounds 4 and 5 shown in Example 6, such that the function of the ligand binding domain of the AR is antagonized.

Yet another embodiment of the invention is a method of antagonizing the effect of an androgen on a function of the ligand binding domain of the AR polypeptide in a prostate cancer cell, the method comprising contacting the cell with a androgen antagonist compound selected from the group consisting of compounds 4 and 5 shown in Example 6, such that the effect of an androgen on a function of the ligand binding domain of the AR polypeptide is antagonized.

Another embodiment of the invention is a composition comprising a compound selected from the group consisting of compounds 4 and 5 shown in Example 6. A related embodiment is a pharmaceutical composition comprising a compound selected from the group consisting of compounds 4 and 5 shown in Example 6. Certain embodiments of the invention include methods of administering these compounds, for example to an individual having a prostate cancer. In view of their similarity with chemical structure of (Casodex), certain methods used in administering this compound can be used in the administration of the novel compounds disclosed herein (see, e.g. U.S. Pat. Nos. 5,985,868, 6,479,063 and 6,506,607 which are incorporated herein by reference).

In a further embodiment of the invention, there are provided articles of manufacture and kits containing materials useful for examining compounds such as AR agonists or antagonists using the methods disclosed herein. The article of manufacture comprises a container with a label. Suitable containers include, for example, bottles, vials, and test tubes. The containers may be formed from a variety of materials such as glass or plastic. The label on the container may indicate directions for either in vivo or in vitro use, such as those described above. The kit of the invention comprises the container described above and a second container comprising a buffer. It may further include other materials desirable from a commercial and user standpoint, including other buffers, diluents, filters, needles, syringes, and package inserts with instructions for use.

DETAILED DESCRIPTION OF THE INVENTION

Figure 1:
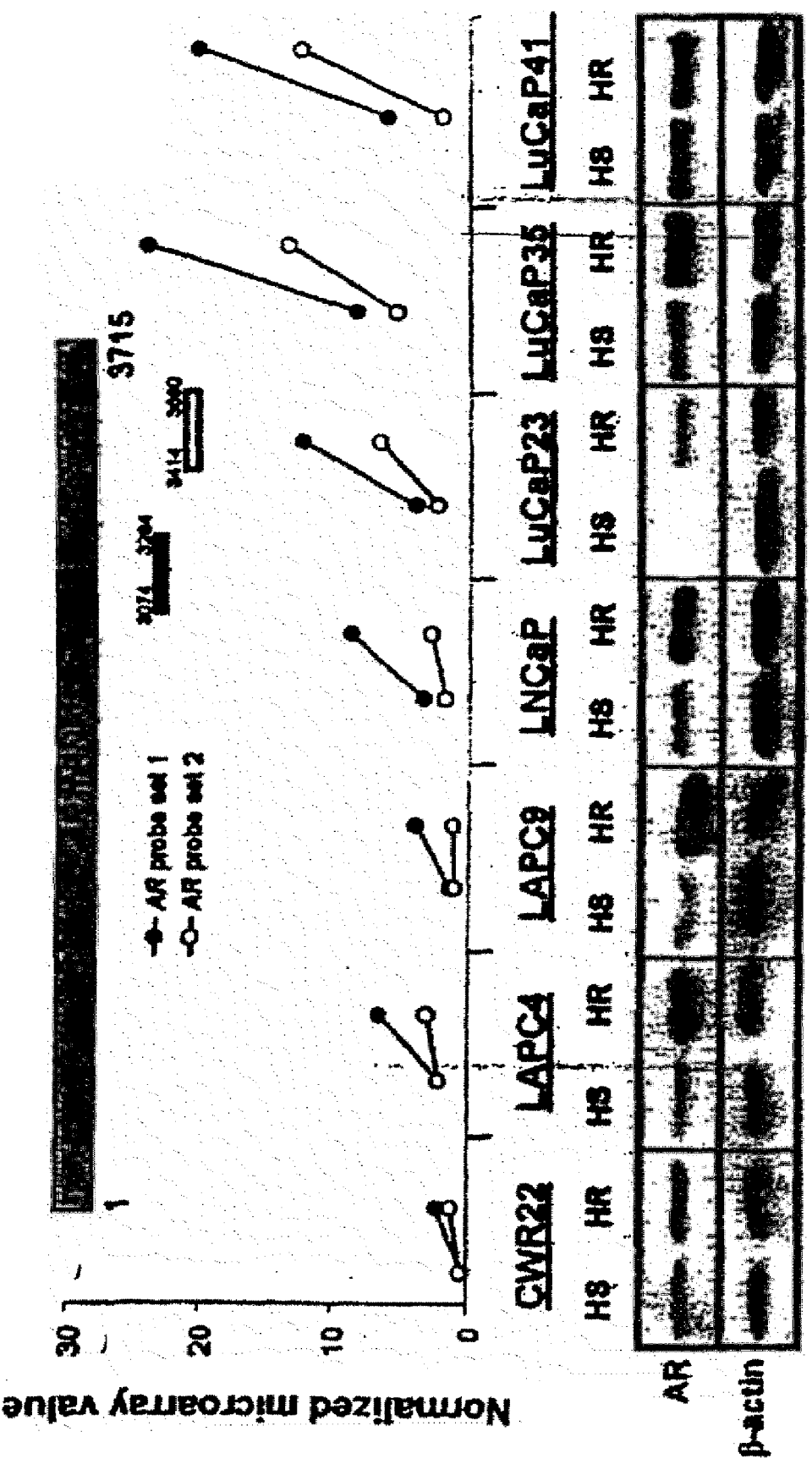
FIG. 1 depicts the results of tests showing expression of AR mRNA in HS And HR Xenografts. Top, normalized microarray values for AR probe sets one and two (Affymetrix IDs 1577 and 1578, respectively) are shown for pools of tumors from each of the fourteen xenografts. Bottom, AR Western blot from one tumor of each xenografts' pool lysed in 2% SDS. AR protein expression in HS LUCaP35 was evident upon longer exposures.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in see Ausubel et al., Current Protocols in Molecular Biology, Wiley Interscience Publishers, (1995) and Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the term "polynucleotide" means a polymeric form of nucleotides of at least about 10 bases or base pairs in length, either ribonucleotides or deoxynucleotides or a modified form of either type of nucleotide, and is meant to include single and double stranded forms of DNA.

As used herein, the term "polypeptide" means a polymer of at least about 6 amino acids. The term "androgen receptor polynucleotide" means any of the polynucleotides that encode the androgen receptor polypeptide. Such polynucleotides are known to those skilled in the art. For example, see Chang et al., Science 240 (4850), 324-326 (1988). The term "androgen receptor polypeptide" means any of the known androgen receptor polypeptides. For example, see Chang et al, Science 240 (4850), 324-326 (1988). The term "androgen receptor polypeptide variant" means a polypeptide that exhibits AR activity and which has a deletion, insertion or substitution of at least one amino acid in the AR polypeptide amino acid sequence as set forth in Chang et al., Science 240 (4850), 324-326 (1988).

The terms "agonist" and "agonistic" when used herein refer to a molecule which is capable of, directly or indirectly, substantially inducing, promoting or enhancing biological activity or activation of a molecule such as AR. The terms "antagonist" and "antagonistic" when used herein refer to a molecule which is capable of; directly or indirectly, substantially inhibiting biological activity or activation of a molecule such as AR.

"Treatment" or "therapy" refer to both therapeutic treatment and prophylactic or preventative measures.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing tumor burden or volume, the time to disease progression (TIP) and/or determining the response rates (RR).

"Growth inhibition" when used herein refers to the growth inhibition of a cell in vitro and/or in vivo. The inhibition of cell growth can be measured by a wide variety of methods known in the art including those described herein. A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethaine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

"Mammal" for purposes of treatment or therapy refers to any animal classified as a mammal, including humans, domestic and farm animals, and zoo, sports, or pet animals, such as dogs, horses, cats, cows, etc. Preferably, the mammal is human.

The terms "cancer", "cancerous", or "malignant" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, ovarian cancer, colon cancer, colorectal cancer, rectal cancer, squamous cell cancer, small-cell lung cancer, non-small cell lung cancer, Hodgkin's and non-Hodgkin's lymphoma, testicular cancer, esophageal cancer, gastrointestinal cancer, renal cancer, pancreatic cancer, glioblastoma, cervical cancer, glioma, liver cancer, bladder cancer, hepatoma, endometrial carcinoma, salivary gland carcinoma, kidney cancer, liver cancer, prostate cancer, vulval cancer, thyroid cancer, hepatic carcinoma and various types of head and neck cancer.

Compositions of the invention can be combined with a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration.

Therapeutic compositions of the invention can be prepared by mixing the desired molecule having the appropriate degree of purity with optional pharmaceutically acceptable carriers, excipients, or stabilizers (see, e.g. Remington: The Science and Practice of Pharmacy, 19$^{th}$ Edition, Gennaro (ed.) 1995, Mack Publishing Company, Easton, Pa.) in the form of lyophilized formulations, aqueous solutions or aqueous suspensions. Acceptable carriers, excipients, or stabilizers are preferably nontoxic to recipients at the dosages and concentrations employed, and include buffers such as Tris, HEPES, PIPES, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; sugars such as sucrose, mannitol, trehalose or sorbitol; salt-forming counter-ions such as sodium; and/or non-ionic surfactants such as TWEEN™, PLURONICS™ or polyethylene glycol (PEG).

The invention is based on the discoveries disclosed herein that a modest (2-5 fold) increase in androgen receptor (AR) mRNA in prostate cancer cells was the only expression change consistently associated with developing resistance to antiandrogen therapy. This increase in AR mRNA and protein was both necessary and sufficient to convert prostate cancer growth from a hormone sensitive to hormone refractory stage, and was dependent on a functional ligand-binding domain. Furthermore, AR antagonists displayed agonist activity in cells with increased AR levels, and this antagonist/agonist conversion was associated with alterations in the pattern of coactivators and corepressors recruited to the promoter of AR target genes. Increased levels of AR confer resistance to antiandrogens by amplifying signal output from low levels of residual ligand and altering the normal response to antagonists. The findings provide insight toward the design of novel antiandrogens.

One embodiment of the invention disclosed herein is a method of testing compounds for an effect on a mammalian prostate cancer cell comprising contacting the compound to be tested with a the mammalian prostate cancer cell, wherein the mammalian cancer cell is selected for the test because it expresses an exogenous wild type androgen receptor (AR) polynucleotide that encodes the AR polypeptide such that the levels of mRNA in the cell that encode the AR polypeptide or the AR polypeptide are at least about 2 fold higher than normal/endogenous AR mRNA levels in a mammalian prostate cell; and then comparing one or more characteristics of the mammalian prostate cancer cell to which the compound was administered with the same one or more characteristics of a control mammalian prostate cancer cell to which the compound has not been administered, wherein a difference in one or more of the one or more characteristics indicates that the compound has an effect on the mammalian prostate cancer cell.

A test compound which binds AR may then be further screened for the inhibition of a specific physiological activity (e.g. tyrosine kinase activity). Such an embodiment includes, for example determining whether said test compound inhibits the signaling of AR by utilizing molecular biological protocols to create recombinant contracts whose enzymological and biological properties can be examined directly. Enzymology is performed for example, by measuring tyrosine kinase activity in vitro or in ARS expressing cells using standard assays.

Certain discoveries and physiological processes associated with the invention are discussed below. In addition, in the examples below, certain compounds useful for example in inhibiting prostate cancer cell growth are described. Methods for making and using these compounds are further disclosed herein.

To examine the range of HR mechanisms in a relatively unbiased manner, we performed global gene expression profiling on seven "isogenic" hormone sensitive (HIS) and HR human prostate cancer xenograft pairs (14 total xenografts). All HR sublines were derived directly from their HS parental lines by passage in castrated mice and compared with HS tumors with similar passage numbers in intact mice.[23-26] The microarray dataset was analyzed using a number of bioinformatic strategies, including unsupervised and supervised learning. First, we asked if any subgroups of HR prostate cancer could be identified using an unsupervised hierarchical clustering algorithm. The following procedure was followed: (a) Seven 0.5 cm$^3$ tumors from each xenograft, grown in either intact (HS) or castrated (HR) mice, were pooled and total RNA was extracted to generate a single sample. After processing, the cRNA was hybridized to the Affymetrix U95A chip and the microarray data was analyzed by Microarray Suite. Background elements which did not significantly vary (standard deviation<1000 and coefficient of variation<1) or were not detected in any of the samples (defined as perfect match hybridization not significantly different than mismatch control signal intensity) were filtered out. The remaining elements, representing 1,056 genes, were then used by an unsupervised learning algorithm to generate a hierarchical clustering diagram. (b) The microarray data, obtained as described in (a), was reanalyzed using Microarray Suite whereby each pair was condensed into a single dataset that represents the ratio in expression between each HS xenograft and its HR counterpart. In addition, using a number of parameters as defined by Microarray Suite software such as fold-change, absolute signal intensity and the confidence in each probe set given by perfect match/mismatch ratios, elements from the condensed dataset were assigned an independent designation of increase (I), marginal increase (MD, no change (NC), marginal decrease (MD) or decrease (D). Elements assessed as NC in all of the xenograft pairs were filtered out to generate a list of 3,774 genes that was then used by an unsupervised learning algorithm to generate a hierarchical clustering diagram. (c) Each of the designations described in (b) was assigned a value ranging from +1 (I) to −1 (D) and a score for each element was produced by summing the values across each of the seven HS/HR xenograft pairs. This testing showed that each HR xenograft clustered with its HS counterpart consistent with the fact that these pairs are isogenic.

Since xenograft-specific expression signatures are likely to obscure gene expression changes responsible for the HS-to-HR transition,[27] we condensed each HS/HR pair into a single dataset representing fold-change in expression. Again, no closely related subgroups emerged, suggesting either that different mechanisms were responsible for the HS-to-HR transition in each xenograft or that any common mechanism involved too few genes to influence the clustering pattern. We explored the latter possibility using an algorithm to identify any elements that consistently changed during the HS-to-HR transition. Remarkably, out of 12,559 probe sets, only one—directed against the AR cDNA—was differentially expressed in all seven HS/HR pairs (FIG. 1, top). Notably, the second highest ranked probe set, upregulated in five of seven pairs, was also directed against AR. Consistent with the RNA data, immunoblots showed higher levels of AR protein in HR tumors than their parental HS counterparts (FIG. 1, bottom). The fold-change in AR protein (based on analysis of individual xenograft tumors) did not perfectly correlate with the fold-change in AR mRNA (based on expression analysis of pools of tumors for each xenograft), possibly due to sample-to-sample variation. Alternatively, post-transcriptional mechanisms may affect steady state AR protein levels.[28] Nonetheless, these data raise the possibility of a common final mechanism of resistance to hormone therapy.

To determine if increased AR protein concentration plays a causal role in the HS-to-HR transition, we introduced an epitope-tagged wildtype AR cDNA by retrovirus infection into HS LNCaP human prostate cancer cells. A three-fold increase in AR levels in LNCaP-AR cells mimics the expression difference observed in the LNCaP HS/HR pair studied in the microarray experiment. To test whether increased AR expression causes the HS-to-HR transition, we designed two in vitro assays to mimic the clinical circumstances of HR disease. The first measures the ability to grow in low androgen concentrations; the second measures growth in the presence of the antiandrogen bicalutamide. As expected, LNCaP cells infected with the empty vector failed to grow in steroid-depleted, charcoal-stripped serum unless supplemented with 100 pM of the synthetic androgen, R1881. In contrast, LNCaP-AR cells grew in at least 80% lower concentrations of R1881. LNCaP-AR cells were also resistant to bicalutamide.

Next, we asked if increased AR expression was sufficient, in vivo, to confer resistance to hormone therapy achieved through surgical castration using two xenograft models, LNCaP and LAPC4. HS LAPC4 cells were infected with AR lentivirus (demonstrated to express about three-fold more AR protein than vector-infected controls) and then implanted into the flanks of intact or castrated male SCID mice. AR overexpression shortened the latency of tumor formation by more than 50%/o in castrated animals in the LAPC4 and LNCaP models.

We used stable RNA interference to address the reciprocal question of whether the increase in AR expression observed in HR xenografts was necessary for developing resistance to hormone therapy. Knockdown of AR levels in HR LAPC4 cells was achieved using a lentivirus vector expressing a short hairpin RNA (shRNA) against AR cis-linked with a GFP-expression cassette. After implantation into the flanks of castrated male mice, AR shRNA-infected tumors grew more slowly than vector-infected controls. Moreover, those tumors that did grow did not express GFP when compared to vector-infected controls and still expressed AR protein, indicating selection for cells that escaped AR knockdown. Parallel studies of AR knockdown in HR LNCaP sublines gave similar results.

To determine the mechanism by which increased AR levels cause HR disease, we considered two possibilities: (1) high levels of receptor lead to constitutive activation in the absence of ligand, consistent with a recent study of AR[29] (a ligand-independent model), or (2) high levels of receptor sensitize the cell to the residual amounts of ligand remaining after testosterone lowering therapy (a ligand-dependent mass action model). To distinguish between these models, we introduced two AR mutations, N705S and R752Q, independently into the LBD to selectively impair ligand-binding without interfering with ligand-independent functions. N705S is associated with complete androgen insensitivity syndrome, whereas R752Q is found in patients with partial androgen insensitivity syndrome.[30]

Details of the experimental procedure were as follows: Mutant or wildtype AR constructs were transfected into AR-null cells (COS 7) and androgen-starved for 48 h. Cells were then incubated with increasing amounts of $^3$H-R1881 in the presence or absence of 100-fold excess of cold R1881 and bound ligand was measured by scintillation counting. LNCaP cells expressing the various AR LBD or genotropic mutants were assayed for HR growth in vitro using either the low-androgen sensitization or antagonist resistance assay as previously described above. All experiments were done in duplicate. $1\times10^6$ LNCaP cells overexpressing the various AR cDNAs (n=10) or a vector control (n=10) were implanted into the flanks of castrated male SCID mice and tumor volume (±SEM) was measured over time. Confocal immunofluorescence was performed with a FLAG-specific antibody on LNCaP cells stably expressing FLAG-tagged, triple point mutant, K618, 632, 633M (ΔNLS) or wildtype AR.

As expected, both mutations impaired ligand-binding in a radiolabeled R1881-binding assay. Consistent with disease severity, R752Q retained low levels of ligand-binding and transcriptional activity in a reporter assay, and serves as an internal control to ensure proper folding of at least one LBD mutant. Overexpression of either LBD mutant AR construct in LNCaP cells, even at levels approximately 10-fold higher than endogenous AR, failed to promote HR growth at levels beyond the vector control in low androgen media, in the presence of bicalutamide or in surgically castrated mice. These data establish that AR must bind ligand to confer HR growth and imply that a modest increase in receptor concentration permits AR to utilize the lower levels of androgens present in castrated patients. This conclusion also suggests that the widely used term "androgen-independent" may be a misleading description of HR prostate cancer.

The availability of these in vitro assays for AR function offered an opportunity to address the additional question of whether AR induces the HS-to-HR transition through genotropic or non-genotropic functions. Deletion of the nuclear localization signal (NLS) blocked nuclear translocation and abolished HR growth in low concentrations of androgen or in the presence of bicalutamide. Similar results were obtained using a second AR mutant V581F that lacks DNA binding activity.[31] Finally, deletion of the polyproline region of AR reported to bind the SH3 domain of Src (ΔP AR)[32] had no inhibitory effect on AR function in these assays. Therefore, the previously reported non-genotropic effects of AR on bone growth and prostate cancer cell survival[32-34] are unlikely to play a role in resistance to antiandrogen therapy.

The ligand-binding mutagenesis studies provide evidence for a mass action model to explain resistance to androgen-lowering hormone therapy. If this mechanism is the sole cause of resistance, then suprapharmacologic concentrations of bicalutamide should overcome the excess levels of AR and block transcriptional activity. Surprisingly, we observed the opposite phenomenon when we examined the effects of high-dose bicalutamide on prostate specific antigen (PSA) expression in cells expressing excess AR. Bicalutamide showed typical antagonist activity in parental LAPC4 cells, as measured by inhibition of PSA mRNA and protein expression, but functioned as an agonist in LAPC4 cells expressing increased levels of AR. The antagonist-to-agonist conversion was not unique to bicalutamide or to the LAPC4 cell line, since similar results were observed using other AR antagonists such as cyproterone acetate and flutamide. Similar results were observed with LNCaP cells. In addition, increased AR levels conferred responsiveness to noncanonical ligands such as estrogen, reminiscent of the effects of the T877A AR LBD mutation in LNCaP cells.[8]

Details of the above high-dose testing were as follows: LAPC4 cells over expressing AR or a GFP control were androgen-starved for 5 days with charcoal-stripped serum and then challenged with bicalutamide or cyproterone acetate or flutamide for 96 hour. PSA and β-actin message was assayed using semi quantitative RT-PCR. Secreted PSA after 48 hour challenge with bicalutamide or 17β-estradiol was measured via ELISA. LNCaP cells stably infected with an AR-expressing or control virus (Neo) was androgen-starved for 5 days and then challenged for 48 hours with bicalutamide. PSA and β-actin were then measured. LNCaP cells stably infected with the AR-expressing virus or the vector control were starved for 5 days and then challenged with either vehicle, 10 μM bicalutamide, 100 pM R1881 or 1 nM DHT. After 1 hour, cells were harvested and processed for chromatin iummunoprecipitation.[21]

To determine if the above-described conversion was peculiar to the PSA gene or was true for other androgen-regulated genes, we conducted a microarray experiment LNCaP cells infected with an AR-expressing retrovirus or the empty-vector control were challenged with increasing doses of R1881 or 10 μM bicalutamide and then processed for hybridization to the Affymetrix U133A chip. Bicalutamide induced the expression of 48 probe sets (defined as 2-fold increase, P<0.05, 500 minimum expression) in LNCaP-AR cells, whereas no elements were significantly upregulated in control cells. The list was comprised mostly of androgen-regulated genes including the well known members, PSA and kallikrein 2 (KLK2)[35]. (See the TABLE at the end of this description for a complete list of the genes tested). However, bicalutamide induced only a subset (<10%) of the total number of androgen-regulated genes (>600 probe sets). Upon closer examination, the bicalutamide-induced genes overlapped, for the most part, with the most highly induced, androgen-responsive genes. Consistent with this, unsupervised hierarchical clustering of the samples grouped the profile of genes induced by 10 μM bicalutamide most closely with those induced by low doses (10-30 pM) of R1881. Together, these data suggest that increased AR expression globally converts antagonists to weak agonists, and therefore leads to the induction of only the most androgen-sensitive genes.

To address the mechanism by which bicalutamide gains agonist properties in the setting of increased AR levels, we performed chromatin immunoprecipitation experiments to define the components of the AR transcription complex on the promoters of two genes, PSA and KLK2, activated by bicalutamide in the microarray experiment. After exposure to the classic agonists R1881 or dihydrotestosterone, AR and polymerase II were recruited to both promoters regardless of AR level as expected from prior work.[21,36] AR was also recruited to both templates after exposure to bicalutamide in vector and AR-overexpressing cells, but polymerase II was present only in the setting of excess AR. However, in AR-overexpressing cells, the repertoire of coactivators recruited to these promoters by bicalutamide was more limited (e.g. SRC1 and not AIB1) when compared with R1881 or dihydrotestosterone. We also examined the effect of increased AR levels on promoter occupancy by corepressors. As expected, NCoR was recruited to both promoters in parental cells following bicalutamide treatment without evidence of histone acetylation or polymerase II recruitment. However, NCoR recruitment was reduced (PSA promoter) or absent (KLK2 promoter) after bicalutamide treatment in cells with increased AR protein levels. Therefore, a modest change in the level of AR protein can shift the relative abundance of coactivators or corepressors assembled on the promoters of AR target genes, with resultant effects on transcriptional activity.

The surprising result from our expression profiling was the universal upregulation of AR mRNA in all the HR xenograft models, a finding likely to have clinical relevance based on surveys of AR levels in patient material.[7,37] AR gene amplification could clearly result in increased AR levels, but this occurs in a minority of patients and cannot be invoked as the explanation for our xenograft findings, since there was no increase in AR copy number during the HS-to-HR transition.[38] Studies of AR gene regulation have implicated AR itself as a positive acting transcription factor that binds the AR gene and leads to increased AR mRNA levels.[39] Therefore, other mechanisms postulated to give increased AR activity, such as increased kinase pathway signaling (ErbB2, Ras, MAPK) or altered coactivator/corepressor ratios, may also lead to increased AR mRNA levels, albeit indirectly. Thus, any one of a number of primary molecular events that alter AR activity could cause an increase in AR mRNA, suggesting a final common pathway for escape from standard hormone therapy.

One caveat is that our conclusions about AR are based on studies of HS xenograft models, nearly all of which have been derived from men with HR disease. The question of how HS growth is "restored" when such tumors are explanted into intact male mice is a long-debated paradox in the prostate cancer field, and the mechanism remains unknown. We previously provided evidence that such explants contain a mixture of HS and HR clones, and that HR sublines develop through clonal expansion under the selective pressure of androgen deprivation.[40] The HS clones that evolve from such explants may be HS only in relative terms, reflecting a transition state in the continuum between truly hormone-naive prostate cancer (no prior exposure to antiandrogen therapy) and full blown HR disease. It remains to be determined whether AR upregulation is sufficient to confer HR growth to hormone-naïve cells. Newer transgenic or knockout models of murine prostate cancer may provide an opportunity to address this question in a "cleaner" experimental system.[41,42]

Figure 2:
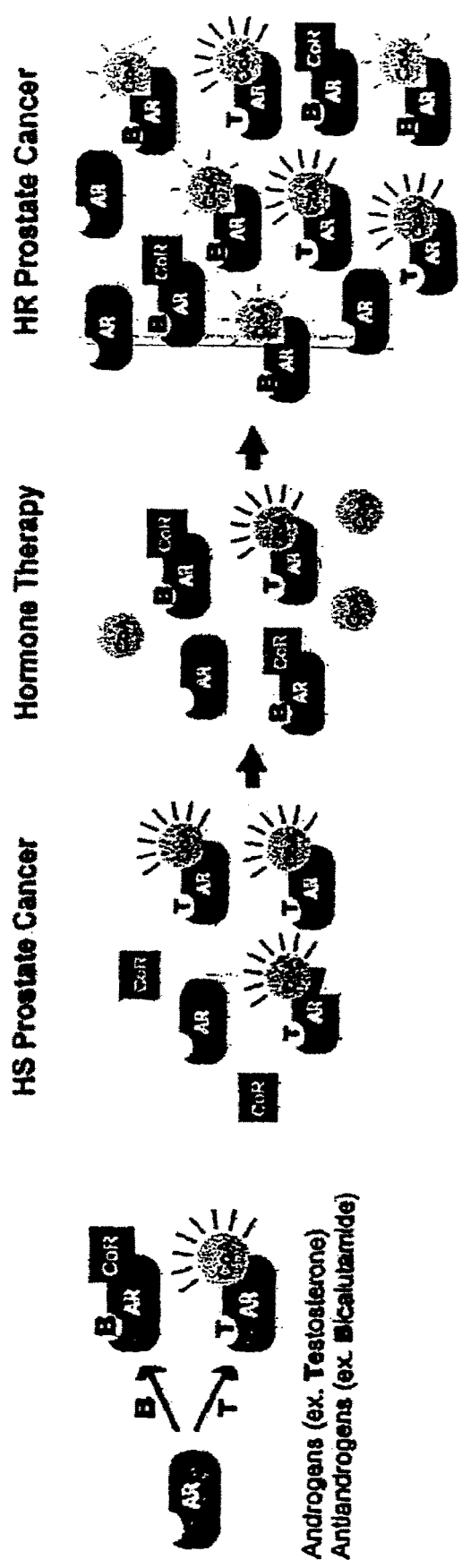
FIG. 2 diagrammatically depicts a model of prostate cancer progression. Hormone therapy, consisting of androgen-lowering drugs and competitive AR antagonists, decreases the number of active receptors leading to a clinical response (HS disease). Failure of therapy (HR disease) results from increased receptor level which inverts the response to antagonists and amplifies the response to all ligands—residual androgens, antagonists and other steroids.

The simplest model to explain how increased expression of AR can confer resistance to anti-androgen therapy is mass action. According to this model, the 3-5 fold increase in receptor levels observed in our xenograft models can compensate for low ligand levels and restore AR signaling. However, the fact that increased receptor levels cause antagonists to function as agonists suggests another level of complexity. Our comparison of genes induced by bicalutamide to those induced by a range of androgen doses indicates that antagonists function as weak agonists in the setting of increased AR levels. Comparative analysis of the transcription complex assembled on the promoters of AR target genes revealed a potential mechanism. Specifically, a more limited repertoire of coactivators is recruited to AR target genes after stimulation with bicalutamide, suggesting that suboptimal ligands cannot assemble the optimal array of cofactors for maximal transcriptional activity (See FIG. 2). Because steroid receptor-antagonist complexes adopt a variety of conformations,[43,44] antagonist-bound AR may be unable to bind the full complement of coactivator machinery.

The molecular basis for loss of antagonism is less apparent. Previous work has demonstrated that the agonist versus antagonist response of nuclear receptors like ER is altered by increased expression of coactivators (increased SRC1) or by decreased expression of corepressors (decreased NCoR).[45,46]

Our data establish that increased expression of the nuclear receptor itself causes a similar outcome, perhaps by upsetting the balance of corepression and coactivation in the cell. Additional experiments examining each of these components are required to sort through these or alternative explanations.

The clinical relevance of antagonist/agonist conversion should also be considered. About 30% of men whose disease progresses during treatment with AR antagonists experience a paradoxical fall in serum PSA levels when the antagonist is discontinued, called anti-androgen withdrawal syndrome.[47] One proposed mechanism is mutation in the AR gene, based on the fact that flutamide functions as an agonist in cells expressing the T877A AR mutation.[8] Although compelling, this mechanism cannot account for all cases because recent estimates of the frequency of AR mutations in HR patients are too low.[5] Our findings suggest that patients with antiandrogen withdrawal syndrome may be those with the highest level of AR upregulation.

Perhaps the most important implication of the present invention is toward the development of novel antiandrogens. The fact that an intact LBD is required for AR to cause resistance to hormone therapy provides compelling rationale for the design of novel antagonists that exploit existing knowledge of this well defined binding pocket.[48] Because AR action appears to be mediated exclusively through genotropic mechanisms, one can also envision drugs that prevent AR nuclear translocation or impair assembly of AR transcription complexes on target genes. Finally, it will be important to determine if the mechanisms of antiandrogen resistance implicated here have relevance for other hormone-dependent diseases such as breast cancer.

Host cells, such as prostate cancer cells can be transfected or transformed with expression or cloning vectors described herein for the expression of the human AR proteins and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

A wide variety of methods of transducing mammalian cells are known in the art, for example, using reagents and methods such as viral vectors (e.g. the retroviral vectors disclosed in the Examples below), lipids (e.g. lipofection), $CaPO_4$ and electroporation etc. Depending on the host cell used, transformation is performed using standard techniques appropriate to such cells. The calcium treatment employing calcium chloride, as described in Sambrook et al., supra or electroporation is generally used for prokaryotes or other cells that contain substantial cell-wall barriers. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*. 185:527-537 (1990) and Mansour et al., *Nature* 336:348-352 (1988).

Suitable host cells for cloning or expressing the AR DNA in the vectors herein include various prostate cancer cell lines such as LNCaP lines, DU145 and TsuPr1, other transfectable or transducible prostate cancer cell lines, primary cells (PrEC), as well as a number of mammalian cells routinely used for the expression of recombinant proteins (e.g., OS, CHO, 293, 293T cells).

The nucleic acid (e.g., cDNA or genomic DNA) encoding AR may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The AR proteins may be produced recombinantly not only directly, but also as a fusion polypeptide with a heterologous polypeptide (e.g., the FLAG tag disclosed herein), which may be a signal sequence or other polypeptide having a specific cleavage site at the N-terminus of the mature protein or polypeptide. In general, the signal sequence may be a component of the vector, or it may be a part of the AR DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors typically contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. A wide range of host-vector systems suitable for the expression of AR are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, AR can be expressed in prostate cancer and non-prostate cell lines, including for example LNCaP, 293, 293T, rat-1, NIH 3T3 and TsuPr1. The host-vector systems of the invention are useful for the production of an AR protein or fragment thereof. Such host-vector systems can be employed to study the functional properties of AR and AR mutations or analogs.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

Examples of suitable selectable markers for mammalian cells are those that enable the identification of cells competent to take up the AR nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 (Stinchcomb et al., *Nature*, 282:39 (1979); Kingsman et al., *Gene*, 7:141 (1979); Tschemper et al., *Gene*, 10:157 (1980)). The trp1 gene provides a selection marker for a mutant strain of yeast lacking the ability to grow in tryptophan, for example, ATCC No. 44076 or PEP4-1 (Jones, *Genetics*, 85:12 (1977)).

Additional details regarding the practice of the invention are as follows: Oligonucleotide U95A and U133A gene arrays were purchased from Affymetrix. Charcoal-stripped dextran-treated fetal bovine serum was obtained from Omega Scientific. Bicalutamide was obtained from the UCLA Investigational Drug Pharmacy and dissolved in acetone. Cold and $^3$H-R1881 were obtained from NEN Life Sciences. AR antibody N-20 (Santa Cruz) and Flag antibody M2 (Sigma) were used in the immunoblot assays. Secreted PSA was measured by ELISA (American Qualex). Protein extracts were prepared in high detergent buffer (2% SDS) to ensure total cell lysis.

Typical DNA constructs were prepared as follows: pCSUACG (U6-shRNAαAR; CMV-GFP) was constructed by ligating the BamHI/EcoRI digests of pCSCG and the U6-shRNAαAR PCR product. The U6-shRNAαAR PCR was performed using a hU6-containing plasmid at a 60° C. annealing temperature with suitable primers: pCSCA (CMV-AR) was created by subcloning the XhaI fragment of pSRα-AR into the NheI site of pCSCG. AR mutants were made by standard PCR-based site-directed mutagenesis using the QuikChange Kit (Stratagene). □NLS contains three point mutations (K618M, K632M, K633M) previously shown to disrupt nuclear import.[49] □Pro contains a deletion of amino acids 372-381, based on prior work.[32] ARR$_2$Pb-Luciferase was kindly provided by Robert Matusik (Vanderbilt). PSA RT-PCR was also performed using suitable primers.

Details of typical In vitro and In vitro Growth experiments are as follows: LNCaP (ATCC) and LAPC4 cells were maintained in Iscove's medium supplemented with 10% fetal bovine serum. LNCaP-AR and LNCaP-vector were derived by infection with the pSR□-AR or pSR□ retrovirus, respectively, and selection in 500 ng/ml of G418. LNCaP-AR, LNCaP-vector, LAPC4AR, and LAPC4-vector in other experiments were derived by infection with the pCSCA or pCSC lentivins, respectively, without selection (>90% infection). For in vitro experiments, LNCaP or LAPC4 cells stably infected with different constructs were androgen-starved by growth in charcoal-stripped serum for 3-5 d. $5 \times 10^4$ cells were plated per well in media containing 10% charcoal-stripped serum supplemented with various concentration of R1881 or in media containing 10% full serum with various concentration of bicalutamide. Colonies were visualized with crystal violet staining 2 weeks later. In vivo tumorigenicity was measured by injection of $5 \times 10^5$ LAPC4 or $1 \times 10^6$ LNCaP cells in 1100 μl of Matrigel (Collaborative Biomedical) subcutaneously into the flanks of intact or castrated male SCID mice. Tumor size was measured weekly in three dimensions using caliber as described.[26] AR knockdown was performed by infection of HR LAPC4 with shRNA AR lentivirus.

Tumors which grew in castrated mice were explanted, and analyzed by flow cytometry for the percentage of GFP-positive cells. All mouse experiments were performed in compliance with the guidelines of the Animal Research Committee (ARC) of the UCLA.

HS and HR xenograft pairs for the microarray study were collected from three institutions. LUCaP23, 35, and 41 were developed at University of Washington; CWR22 was developed by Case Western Reserve University and kindly provided by University of North Carolina at Chapel Hill; LAPC4 and 9 were developed at the University of California at Los Angeles; LNCaP was purchased from ATCC and implanted into mice. The HS xenografts were either grown in intact nude mice or SCID male mice, and their HR counterparts were developed by serial passage in castrated male mice. Microarray experiments were performed and data analyzed according to manufacture's instructions (Affymetrix). We extracted total RNA from a pool of two to eight tumors with comparable sizes and serum PSA levels for each xenograft using TriReagent Molecular Research Center) and RNeasy (Qiagen). For each sample, 15 µg of total RNA was used to generate double stranded cDNA and the cRNA was transcribed with biotin-labeled nucleotides (ENZO Diagnostics). The cRNA was fragmented and hybridized to U95A microarray (Affymetrix). Scanned images were used for absolute and comparison analysis (Affymetrix manual). The microarray data were generated through the Genespring program (Silicon Genetics).

Details of typical chromatin immunoprecipitation are as follows: LNCaP-AR or LNCaP-vector were androgen-starved and challenged with either vehicle, 100 pM of R1881, 1 nM of DHT, or 10 µM of bicalutamide for 1 hour. Soluble chromatin was prepared after formaldehyde crosslinking and sonication. Specific IgGs against AR, N—CoR, PolII, Ac-H3/4, SRC1, TIF2, AIB1, and PCAF were used to immunoprecipitate protein-bound DNA fragments. After reversing the crosslinking, PCR reactions were performed to amplify the promoter regions of KLK3/PSA or KLK2.[21] Duplicates for bicalutamide or vehicle treatment were averaged and queried for the number of probe sets induced 2-fold, P<0.05 with a minimum expression of 500 in at least one sample. The dataset was analyzed for the number of probe sets that induced a minimum 2-fold increase. The data showed that increased AR expression globally converts antagonists to weak agonists.

Throughout this application, various publications are referenced (within parentheses for example). The disclosures of these publications are hereby incorporated by reference herein in their entireties. In order to facilitate an understanding of various typical aspects of the invention, certain aspects of these incorporated materials are reproduced herein.

The following examples provide an illustration of how the screening method of the present invention was used in the testing, development and identification of new chemical compounds for the treatment of prostate cancer, especially hormone-refractory (androgen-independent) prostate cancer).

There are many compounds which have been reported to be inhibitors of the ligand binding domain (LBD) androgen receptor (AR). Several have been used as drugs to treat prostate cancer, e.g., bicalutamide (Casodex) 1, which is the current drug of choice for treatment of:

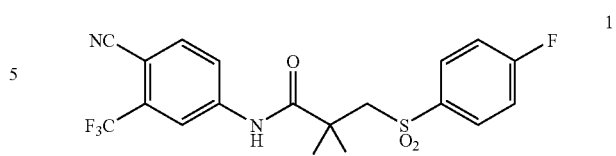

prostate cancer. Several more potent binders of the AR LBD have been identified, e.g., the thiohydantoins, RU59063 2 and BTID, 3 (see, e.g. Teutsch et al., *J. Steroid Biochem. Molec. Biol.* 1994, 48, 111-119 and Van Dort et al., *J. Med. Chem.* 2000, 43, 3344-3347). We decided to carry out a study using the screening method of the present invention to identify novel analogues of compounds such as 2 and 3 which would have other alkyl groups with final polar functionality in place of the 4-hydroxybutyl group (R in 2 and 3) which might form much stronger interactions, and even in some cases covalent interactions, with the various polar amino acid side chains of the LBD of the AR. Thus the state of the art was that some strong binders had been discovered but they had not been yet developed into prostate cancer drugs.

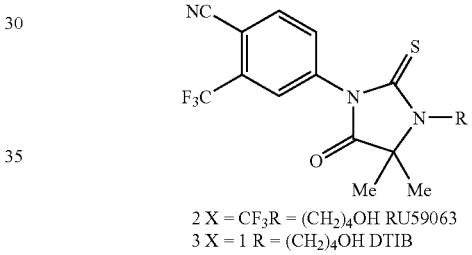

2 X = CF₃ R = (CH₂)₄OH RU59063
3 X = I R = (CH₂)₄OH DTIB

We have prepared a series of compounds 4 based on the general structure 2 and have carried out initial screening using the method of the present invention and additional biological testing which shows that these compounds inhibit the growth of a prostate cancer cell line, including hormone-sensitive and hormone-refractory variants. The biological data allows us to measure both agonist and antagonist effects and we find that the best compounds are pure antagonists, namely they bind strongly to the LBD of the AR and shut down the natural process of active cancer growth. In particular the 4-azido-phenyl derivative 5 has shown the best antagonist effects without any strong agonist effects.

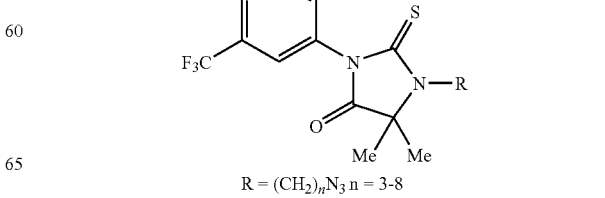

R = (CH₂)ₙN₃ n = 3-8

-continued

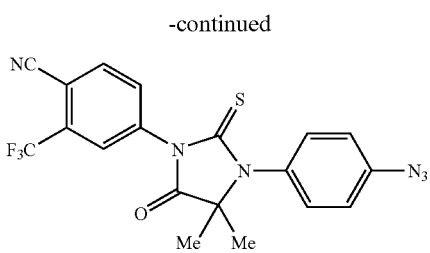

The preferred sequence for the chemical synthesis of these compounds is shown below. The commercially available aniline 6 is converted in one step into the isothiocyanate 7. Commercially available acetone cyanohydrin 8 is converted into the two cyanoamines 10ab by reaction with the amines 9a (n=3-8) and the aniline 9b. Addition of 10ab to 7 followed by treatment with mild acid produces the desired thiohydantoins 4 (n=3-8) and 5 in good yield.

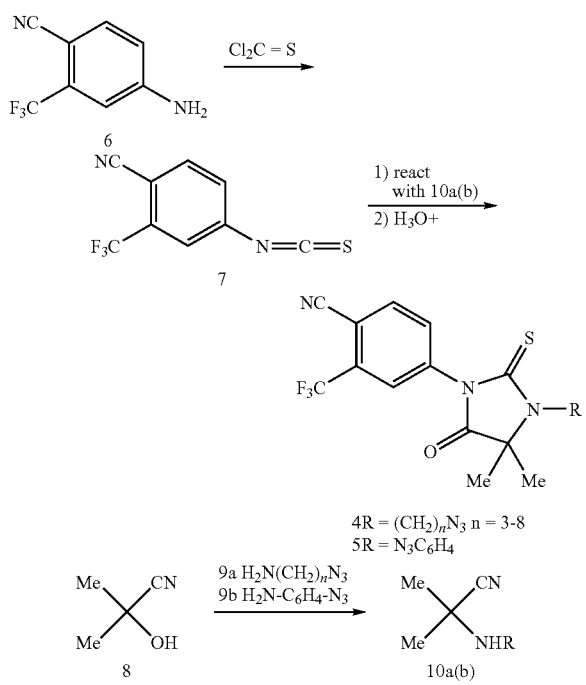

These compounds 4 and 5 show remarkable anti-prostate cancer activity. The biological testing was carried out by measurement of the amount of prostate-specific antigen (PSA) produced by LNCaP cells. The $IC_{50}$ values of 4 and 5 for PSA expression are ten-fold lower that that for bicalutamide (2-3 times stronger) and the compounds seem to be full antagonists. Therefore they offer the potential for a better drug for the treatment of prostate cancer, namely they antagonize the effect of androgens on the AR and thus should greatly slow the progression of prostate cancer.

As shown above, we have prepared the compounds 4 and 5 and carried out the initial set of biological assays (including initial screening using the method of the present invention) that show their potent binder and antagonist ability. This exciting set of compounds is relatively simple to synthesize and already have more potential man the well known heavily used antiprostate cancer drug Casodex.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention. However, the invention is only limited by the scope of the appended claims.

TABLE

| Affy ID | GenBank ID | Affy ID | GenBank ID |
| --- | --- | --- | --- |
| 212005 | AL582808 | 206205 | NM_022782.1 |
| 213017 | NM_138340 | 221965 | NM_022782 |
| 201662 | D89053.1 | 208309 | NM_006785.1 |
| 216323 | XM_054284 | 214087 | NM_002465 |
| 211689 | AF270487.1 | 211548 | J05594.1 |
| 205102 | NM_005656 | 205040 | NM_000607.1 |
| 215990 | S67779.1 | 205041 | NM_000607.1 |
| 203356 | NM_014296 | 220954 | NM_013440.1 |
| 222201 | AB037736.1 | 206178 | NM_000929.1 |
| 221272 | NM_030806.1 | 214443 | NM_006505.1 |
| 222121 | NM_015595 | 218782 | NM_014109.1 |
| 212665 | NM_015508 | 205924 | BC005035.1 |
| 209389 | M15887.1 | 201975 | NM_002956.1 |
| 204560 | NM_004117.1 | 201562 | NM_003104 |
| 210892 | BC004472.1 | 216920 | M27331.1 |
| 219312 | NM_023929.1 | 215806 | M13231.1 |
| 219476 | NM_024115.1 | 209813 | M16768.1 |
| 210339 | BC005196.1 | 211144 | M30894.1 |
| 209854 | NM_005551 | 201108 | NM_003246 |
| 204583 | U17040.1 | 222118 | AK023669.1 |
| 204582 | NM_001648 | 219555 | NM_018455 |
| 212789 | XM_166201 | 219551 | NM_018456.1 |
| 205862 | NM_014668.1 | 209053 | BE793789 |
| 201551 | J03263.1 | 209309 | D90427.1 |

BIBLIOGRAPHY

1. Feldman, B. J. & Feldman, D. The development of androgen-independent prostate cancer. *Nat Rev Cancer* 1, 34-45 (2001).
2. Gelmann, E. P. Molecular biology of the androgen receptor. *J Clin Oncol* 20, 3001-15 (2002).
3. Balk, S. P. Androgen receptor as a target in androgen-independent prostate cancer. *Urology* 60, 132-8; discussion 138-9 (2002).
4. Taplin, M. E. et al. Selection for androgen receptor mutations in prostate cancers treated with androgen antagonist. *Cancer Res* 59, 2511-5 (1999).
5. Taplin, M. E. et al. Androgen receptor mutations in androgen-independent prostate cancer: Cancer and Leukemia Group B Study 9663. *J Clin Oncol* 21, 2673-8 (2003).
6. Visakorpi, T. et al. In vivo amplification of the androgen receptor gene and progression of human prostate cancer. *Nat Genet* 9, 401-6 (1995).
7. Taplin, M. E. et al. Mutation of the androgen-receptor gene in metastatic androgen-independent prostate cancer. *N Engl J Med* 332, 1393-8 (1995).
8. Veldscholte, J. et al. A mutation in the ligand binding domain of the androgen receptor of human LNCaP cells affects steroid binding characteristics and response to antiandrogens. *Biochem Biophys Res Commun* 173, 534-40 (1990).
9. Matias, P. M. et al. Structural basis for the glucocorticoid response in a mutant human androgen receptor (AR(ccr))

derived from an androgen-independent prostate cancer. *J Med Chem* 45, 1439-46 (2002).
10. Craft, N., Shostak, Y., Carey, M. & Sawyers, C. L. A mechanism for hormone-independent prostate cancer through modulation of androgen receptor signaling by the HER-2/neu tyrosine kinase. *Nat Med* 5, 280-5 (1999).
11. Gioeli, D. et al. Androgen receptor phosphorylation. Regulation and identification of the phosphorylation sites. *J Biol Chem* 277, 29304-14 (2002).
12. Kato, S. et al. Activation of the estrogen receptor through phosphorylation by mitogen-activated protein kinase. *Science* 270, 1491-4 (1995).
13. Font de Mora, J. & Brown, M. AIB1 is a conduit for kinase-mediated growth factor signaling to the estrogen receptor. *Mol Cell Biol* 20, 5041-7 (2000).
14. Tremblay, A., Tremblay, G. B., Labrie, F. & Giguere, V. Ligand-independent recruitment of SRC-1 to estrogen receptor beta through phosphorylation of activation function AF-1. *Mol Cell* 3, 513-9 (1999).
15. Gregory, C. W. et al. A mechanism for androgen receptor-mediated prostate cancer recurrence after androgen deprivation therapy. *Cancer Res* 61, 4315-9 (2001).
16. Li, P. et al. Heterogeneous expression and functions of androgen receptor co-factors in primary prostate cancer. *Am J Pathol* 161, 1467-74 (2002).
17. Glass, C. K. & Rosenfeld, M. G. The coregulator exchange in transcriptional functions of nuclear receptors. *Genes Dev* 14, 121-41 (2000).
18. Raffo, A. J. et al. Overexpression of bcl-2 protects prostate cancer cells from apoptosis in vitro and confers resistance to androgen depletion in vivo. *Cancer Res* 55, 4438-45 (1995).
19. McDonnell, T. J. et al. Expression of the proto-oncogene bcl-2 in the prostate and its association with emergence of androgen-independent prostate cancer. *Cancer Res* 52, 6940-4 (1992).
20. Kinoshita, H. et al. Methylation of the androgen receptor minimal promoter silences transcription in human prostate cancer. *Cancer Res* 60, 3623-30 (2000).
21. Shang, Y., Myers, M. & Brown, M. Formation of the androgen receptor transcription complex. *Mol Cell* 9, 601-10 (2002).
22. Zhau, H. Y. et al. Androgen-repressed phenotype in human prostate cancer. *Proc Natl Acad Sci USA* 93, 15152-7 (1996).
23. Wainstein, M. A. et al. CWR22: androgen-dependent xenograft model derived from a primary human prostatic carcinoma. *Cancer Res* 54, 6049-52 (1994).
24. Ellis, W. J. et al. Characterization of a novel androgen-sensitive, prostate-specific antigen-producing prostatic carcinoma xenograft: LuCaP 23. *Clin Cancer Res* 2, 1039-48 (1996).
25. Horoszewicz, J. S. et al. LNCaP model of human prostatic carcinoma. *Cancer Res* 43, 1809-18 (1983).
26. Klein, K. A. et al. Progression of metastatic human prostate cancer to androgen independence in immunodeficient SCID mice. *Nat Med* 3, 402-8 (1997).
27. Perou, C. M. et al. Molecular portraits of human breast tumors. *Nature* 406, 747-52 (2000).
28. Gregory, C. W., Johnson, R. T., Jr., Mohler, J. L., French, F. S. & Wilson, E. M. Androgen receptor stabilization in recurrent prostate cancer is associated with hypersensitivity to low androgen. *Cancer Res* 61, 2892-8. (2001).
29. Huang, Z. Q., Lit J. & Wong, J. AR possesses an intrinsic hormone-independent transcriptional activity. *Mol Endocrinol* 16, 924-37 (2002).
30. Matias, P. M. et al. Structural evidence for ligand specificity in the binding domain of the human androgen receptor. Implications for pathogenic gene mutations. *J Biol Chem* 275, 26164-71 (2000).
31. Lobaccaro, J. M. et al. Molecular modeling and in vitro investigations of the human androgen receptor DNA-binding domain: application for the study of two mutations. *Mol Cell Endocrinol* 116, 137-47 (1996).
32. Migliaccio, A. et al. Steroid-induced androgen receptor-oestradiol receptor beta-Src complex triggers prostate cancer cell proliferation. *Embo J* 19, 5406-17 (2000).
33. Kousteni, S. et al. Nongenotropic, sex-nonspecific signaling through the estrogen or androgen receptors: dissociation from transcriptional activity. *Cell* 104, 719-30 (2001).
34. Manolagas, S. C., Kousteni, S. & Jilka, R. L. Sex steroids and bone. *Recent Prog Horm Res* 57, 385-409 (2002).
35. DePrimo, S. E. et al. Transcriptional programs activated by exposure of human prostate cancer cells to androgen. *Genome Biol* 3, RESEARCH0032 (2002).
36. Masiello, D., Cheng, S., Bubley, G. J., Lu, M. L. & Balk, S. P. Bicalutamide functions as an androgen receptor antagonist by assembly of a transcriptionally inactive receptor. *J Biol Chem* 277, 26321-6 (2002).
37. Edwards, J., Krishna, N. S., Grigor, K. M. & Bartlett, J. M. Androgen receptor gene amplification and protein expression in hormone refractory prostate cancer. *Br J Cancer* 89, 552-6 (2003).
38. Laitinen, S., Karhu, R., Sawyers, C. L., Vessella, R. L. & Visakorpi, T. Chromosomal aberrations in prostate cancer xenografts detected by comparative genomic hybridization. *Genes Chromosomes Cancer* 35, 66-73 (2002).
39. Grad, J. M., Dai, J. L., Wu, S. & Burnstein, K. L. Multiple androgen response elements and a Myc consensus site in the androgen receptor (AR) coding region are involved in androgen-mediated up-regulation of AR messenger RNA. *Mol Endocrinol* 13, 1896-911 (1999).
40. Craft, N. et al. Evidence for clonal outgrowth of androgen-independent prostate cancer cells from androgen-dependent tumors through a two-step process. *Cancer Res* 59, 5030-6 (1999).
41. Ellwood-Yen, K, et al. Myc-driven murine prostate cancer shares molecular features with human prostate tumors. *Cancer Cell* 4, 223-38 (2003).
42. Wang, S. et al. Prostate-specific deletion of the murine Pten tumor suppressor gene leads to metastatic prostate cancer. *Cancer Cell* 4, 209-21 (2003).
43. Shiau, A. K. et al. The structural basis of estrogen receptor/coactivator recognition and the antagonism of this interaction by tamoxifen. *Cell* 95, 927-37 (1998).
44. Norris, J. D. et al. Peptide antagonists of the human estrogen receptor. *Science* 285, 744-6 (1999).
45. Baek, S. H. et al. Exchange of N-CoR corepressor and Tip60 coactivator complexes links gene expression by NF-kappaB and beta-amyloid precursor protein. *Cell* 110, 55-67 (2002).
46. Shang, Y. & Brown, M. Molecular determinants for the tissue specificity of SERMs. *Science* 295, 2465-8 (2002).
47. Schellhammer, P. F. et al. Prostate specific antigen decreases after withdrawal of antiandrogen therapy with bicalutamide or flutamide in patients receiving combined androgen blockade. *J Urol* 157, 1731-5 (1997).
48. Sack, J. S. et al. Crystallographic structures of the ligand-binding domains of the androgen receptor and its T877A mutant complexed with the natural agonist dihydrotestosterone. *Proc Natl Acad Sci USA* 98, 4904-9 (2001).
49. Zhou, Z. X., Sar, M., Simental, J. A., Lane, M. V. & Wilson, E. M. A ligand-dependent bipartite nuclear targeting signal in the human androgen receptor. Requirement for the DNA-binding domain and modulation by NH2-terminal and carboxyl-terminal sequences. *J Biol Chem* 269, 13115-23 (1994).

What is claimed is:

1. A composition of matter comprising a compound having the formula

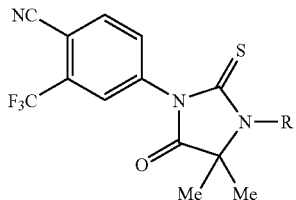

wherein R is $N_3C_6H_4$.

2. A pharmaceutical composition comprising a compound according to claim 1 and a pharmaceutically acceptable carrier for said compound.

3. A method of inhibiting prostate specific antigen production in a mammalian prostate cancer cell, the method comprising contacting said mammalian prostate cancer cell with a sufficient amount of a compound according to claim 1, such that prostate specific antigen production in said mammalian prostate cancer cell is inhibited.

4. A method of inhibiting the growth of a human prostate cancer cell, the method comprising contacting said human prostate cancer cell with an amount of a compound according to claim 1, such that growth of said human prostate cancer cell is inhibited.

5. A method of antagonizing the function of the ligand binding domain of the androgen receptor polypeptide in a prostate cancer cell, said method comprising the step of contacting said prostate cancer cell with a sufficient amount of a compound according to claim 1, such that the function of the ligand binding domain of the androgen receptor is antagonized.

6. A method of antagonizing the effect of an androgen on a function of the ligand binding domain of the androgen receptor polypeptide in a prostate cancer cell, the method comprising the step of contacting said prostate cancer cell with a sufficient amount of a compound according to claim 1, such that the effect of an androgen on a function of the ligand binding domain of the androgen receptor polypeptide is antagonized.

7. A method comprising examining the physiological effect of the compound of claim 1 on a mammalian prostate cancer cell wherein said prostate cancer cell expresses an exogenous wild type androgen receptor polynucleotide that encodes an androgen receptor polypeptide or an androgen receptor polypeptide variant, said cell further comprising an abnormal level of mRNA that encodes said androgen receptor polypeptide or said androgen receptor polypeptide variant when compared to the level of mRNA that encodes said androgen receptor polypeptide or said androgen receptor polypeptide variant in a normal prostate cell, the method comprising:

(a) determining that said abnormal level of mRNA in said prostate cancer cell is at least two fold higher than the level of mRNA in said normal prostate cell;

(b) contacting the compound with said prostate cancer cell to provide a treated prostate cancer cell; and (c) examining one or more physiological characteristics of said treated prostate cancer cell.

8. A method comprising examining the physiological effect of said the compound of claim 1 on a mammalian prostate cancer cell wherein said prostate cancer cell expresses an exogenous wild type androgen receptor polynucleotide that encodes an abnormal level of androgen receptor polypeptide or an abnormal level of androgen receptor polypeptide variant when compared to the level of androgen receptor polypeptide or androgen receptor polypeptide variant encoded by a normal prostate cell the method comprising:

(a) determining that said abnormal level of androgen receptor polypeptide or said abnormal level of androgen receptor polypeptide variant is at least two fold higher than the level of androgen receptor polypeptide or androgen receptor polypeptide variant in said normal prostate cell;

(b) contacting the compound with said prostate cancer cell to provide a treated prostate cancer cell; and (c) examining one or more physiological characteristics of said treated prostate cancer cell.

9. The composition of claim 1, wherein R is

10. The composition of claim 2, wherein the compound is in an amount effective to antagonize a function of a ligand binding domain of an androgen receptor polypeptide in a prostate cancer cell.

11. The composition of claim 2, wherein the compound is in an amount effective to inhibit the growth of hormone refractory prostate cancer cells.

12. A method comprising reacting a compound of Formula 10b

Formula 10b

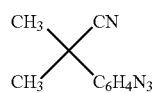

with a compound of Formula 7

Formula 7

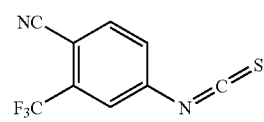

to make the compound according to claim 1.

13. A method comprising mixing the compound according to claim 1 with a pharmaceutically acceptable carrier to make a pharmaceutical composition.

\* \* \* \* \*